United States Patent
Peterson et al.

(12) 
(10) Patent No.: US 6,197,197 B1
(45) Date of Patent: Mar. 6, 2001

(54) METHOD FOR FLUID DELIVERY IN A DIALYSIS CLINIC

(75) Inventors: Michael J. Peterson, Nashville; Richard M. Russell, Brentwood, both of TN (US)

(73) Assignee: Dialysis Systems, Inc., Nashville, TN (US)

( * ) Notice: Subject to any disclaimer, the term of this patent is extended or adjusted under 35 U.S.C. 154(b) by 0 days.

(21) Appl. No.: 09/206,904

(22) Filed: Dec. 7, 1998

Related U.S. Application Data

(63) Continuation-in-part of application No. 09/065,780, filed on Apr. 23, 1998, now abandoned.

(51) Int. Cl.[7] .................................................. B01D 61/20
(52) U.S. Cl. .................... 210/646; 210/232; 210/252; 210/321.71
(58) Field of Search ............................... 210/252, 321.71, 210/232, 236, 646; 138/114, 117, 120, 155, 106, DIG. 3

(56) References Cited

U.S. PATENT DOCUMENTS

| | | |
|---|---|---|
| 3,692,920 | 9/1972 | Santarelli . |
| 3,699,235 | 10/1972 | Wasson et al. . |
| 3,931,452 | 1/1976 | Nilsson . |
| 4,144,165 | 3/1979 | Matz . |
| 4,305,430 | 12/1981 | Svensson . |
| 4,579,879 | 4/1986 | Flynn . |
| 4,620,846 | 11/1986 | Goldberg et al. . |
| 4,655,923 | * 4/1987 | Leone . |
| 4,779,652 | * 10/1988 | Sweeney . |
| 5,015,389 | * 5/1991 | Portillo . |
| 5,165,453 | 11/1992 | Walker . |
| 5,275,724 | * 1/1994 | Bucchianeri . |
| 5,400,828 | 3/1995 | Ziu . |
| 5,522,805 | * 6/1996 | Vancaillie et al. . |
| 5,553,971 | * 9/1996 | Osborne . |
| 5,591,344 | * 1/1997 | Kenley et al. . |
| 5,634,896 | 6/1997 | Bryant et al. . |
| 5,651,893 | 7/1997 | Kenley et al. . |
| 5,685,835 | 11/1997 | Brugger . |

OTHER PUBLICATIONS

Exhibit A (8 pages of photographs of prior art system—undated but admitted to be prior art).

* cited by examiner

*Primary Examiner*—Matthew O. Savage
*Assistant Examiner*—David Sorkin
(74) *Attorney, Agent, or Firm*—Lucian Wayne Beavers Waddey & Patterson

(57) ABSTRACT

A modular fluid transport system is provided for transporting fluids in a dialysis clinic from a fluid source to the dialysis machines. The system includes modular ductwork and modular fluid conduits. The connecting stations may include quick detachable interface manifolds which allow dialysis machines to be easily changed out. The components of the fluid transport system may be heat sterilized. The components of the system may be prefabricated off site and then quickly assembled in the dialysis clinic. Flexibility in the arrangement of equipment within the clinic is provided for.

8 Claims, 13 Drawing Sheets

METHOD FOR FLUID DELIVERY IN A DIALYSIS CLINIC

This application is a continuation in part of U.S. patent application Ser. No. 09/065,780 filed Apr. 23, 1998 now abandoned.

BACKGROUND OF THE INVENTION

The present invention relates generally to a portable system for transporting fluids from a source of purified water or dialysate to individual dialysis machines in a dialysis clinic.

It will be appreciated by those skilled in the art that present systems used for fluid delivery to dialysis machines in dialysis clinic pose problems due to limited space and incidence of bacterial contamination. Furthermore, these systems are installed as permanent fixtures, making them expensive to install, expensive to disinfect, expensive to repair, and expensive to replace. Presently used systems installed as permanent fixtures physically depreciate over time, without the tax advantage of financial depreciation allowed for non-permanent equipment.

The prior art systems provide fluids from a fixed water treatment plant in one part of a building to the dialysis machines in another room. This distance requires that long "runs" be used to transport fluids from the water treatment facility to the dialysis machines. This means that the prior art systems use large runs of piping.

It will be further appreciated by those skilled in the art that bacterial contamination is a common problem in presently available systems. Standard plumbing design and polyvinyl chloride pipes are commonly used. The use of PVC piping and solvent welding methods of joining and fabrication of existing fluid delivery systems results in the creation of cavities which cannot adequately be disinfected by conventional clean in place procedures used by dialysis clinics.

It will be further appreciated that there is a broad range of PVC mixtures utilizing a variety of stabilizers and plasticizers which over time leach into the fluid stream, and that the interior pipe surface becomes pitted and more conducive to trapping bacteria and supporting bacterial growth.

It will be further appreciated by those skilled in the art that present systems require a significant amount of space, restricting mobility within a dialysis clinic and making the use of more heat-resistant yet expensive tubing, such as polytetrafluoroethylene (Teflon®) tubing cost prohibitive. Instead the predominant current practice for dialysate distribution piping makes use of chemical clean in place disinfection in materials (e.g. PVC) which are incompatible with heat disinfection. Furthermore, present systems are piped in permanent structures; chaises or bulky consoles that do not permit easy access, repair or replacement.

It will be further appreciated by those skilled in the art that heat disinfection means are preferable to chemical disinfection means in these systems. Chemical disinfectants presently in use include strong oxidizing agents. Residual disinfectant not adequately flushed from the system poses a hazard to patients. For example, a common chemical disinfectant, formaldehyde, has been shown to cause some repeat dialysis patients to develop antibodies to the N-antigens on the surface of their own red blood cells. The present invention facilitates the use of heat disinfection by providing materials of construction that can be operated at high temperature.

It will be further appreciated by those skilled in the art that, despite the use of chemical disinfectants, present systems still experience problems with bacterial contamination. Regular assay for endotoxin in the system is required. Furthermore, multiple connection points and ready access to those connections makes current systems more susceptible to deliberate tampering by unauthorized personnel.

What is needed then is a system which facilitates heat disinfection and eliminates solvent welded joints. This needed system must eliminate "dead legs" in the system. A "dead leg" is generally defined as a dead end length of pipe of greater than five pipe diameters in length. This needed system must decrease equipment surface area in the dialysis clinic, facilitating disinfection. This needed system must provide replaceable components which are easily installed, repaired, and replaced, yet protected from potential tampering by unauthorized individuals. This needed system must be capable of use without being attached to real property. This needed system must use quick disconnects to permit easy placement of components. This needed system is presently lacking in the prior art.

SUMMARY OF THE INVENTION

A fluid transport system is provided for communicating a source of fluids to at least one fluid-requiring instrument. The system is particularly designed to communicate ultra-pure water and additives to a dialysis machine in a dialysis clinic.

The system includes modular ductwork which includes a plurality of removable ductwork segments defining a secondary containment chamber. A plurality of conduits are received through the ductwork for carrying fluids from the source to the fluid requiring instrument. Any fluids leaking from the conduits are caught in the secondary containment chamber.

Each conduit of the plurality of conduits may be made up of a plurality of removable interconnecting fluid conduit segments. Preferably the system includes interchangeable modules, with each module including modular ductwork made up of a plurality of ductwork segments, and with each module including a plurality of conduit segments which corresponds to the plurality of conduits. Each conduit segment has a detachable coupling on at least one end thereof.

The system may be installed either on the wall of a room, or extending into the interior area of a room. Those portions of the system extending into the interior of a room are supported on columns which preferably include lockable casters to provide mobility of the support columns within the room.

At various locations throughout the system stations are provided for connection of the system to a dialysis machine. Each connecting station preferably includes a first manifold block to which the conduits are directly connected, and a second manifold block which is connected to the first manifold block by a plurality of quick connect couplings. The second manifold block further carries a second plurality of quick connect couplings which are specifically designed for connection to a particular brand and model of dialysis treatment machine. The dialysis treatment machines may be quickly changed by disconnecting the second manifold block from the first manifold block, and replacing the second manifold block with another manifold block having quick connect couplings specifically associated with another type of dialysis machine.

It is therefore an object of the present invention to provide a portable system for transporting fluids from a source of purified water to individual dialysis machines in a dialysis clinic.

Another purpose of the present invention is the provision of a modular fluid transport system for communicating a source of fluids to at least one fluid-requiring instrument.

Still another object of the present invention is the provision of modular fluid transport systems for dialysis clinics, wherein the system is made up of a plurality of interchangeable modules.

And another object of the present invention is the provision of a modular fluid transport system which can be heat sterilized.

Still another object of the present invention is the provision of a fluid transport system having quick connect stations for connection of a dialysis machine or other fluid-requiring instrument.

Another object of the present invention is the provision of a quick connect station for a fluid transport system, wherein the instrument to be connected to the station can be disconnected and replaced without interfering with the flow of fluid through the system.

Another object of the present invention is the provision of methods of installing a fluid transport system for a dialysis clinic.

Numerous other objects, features and advantages of the present invention will be readily apparent to those skilled in the art upon reading of the following disclosure when taken in conjunction with the accompanying drawings.

BRIEF DESCRIPTION OF THE DRAWINGS

FIG. 24 shows integral shut off valves.

DETAILED DESCRIPTION OF THE PREFERRED EMBODIMENTS

THE EMBODIMENTS OF FIGS. 1–12

The structure shown in FIGS. 1–12 is also shown and described in our co-pending U.S. patent application Ser. No. 09/065,780 filed Apr. 23, 1998, the details of which are incorporated herein by reference.

Figure 1:
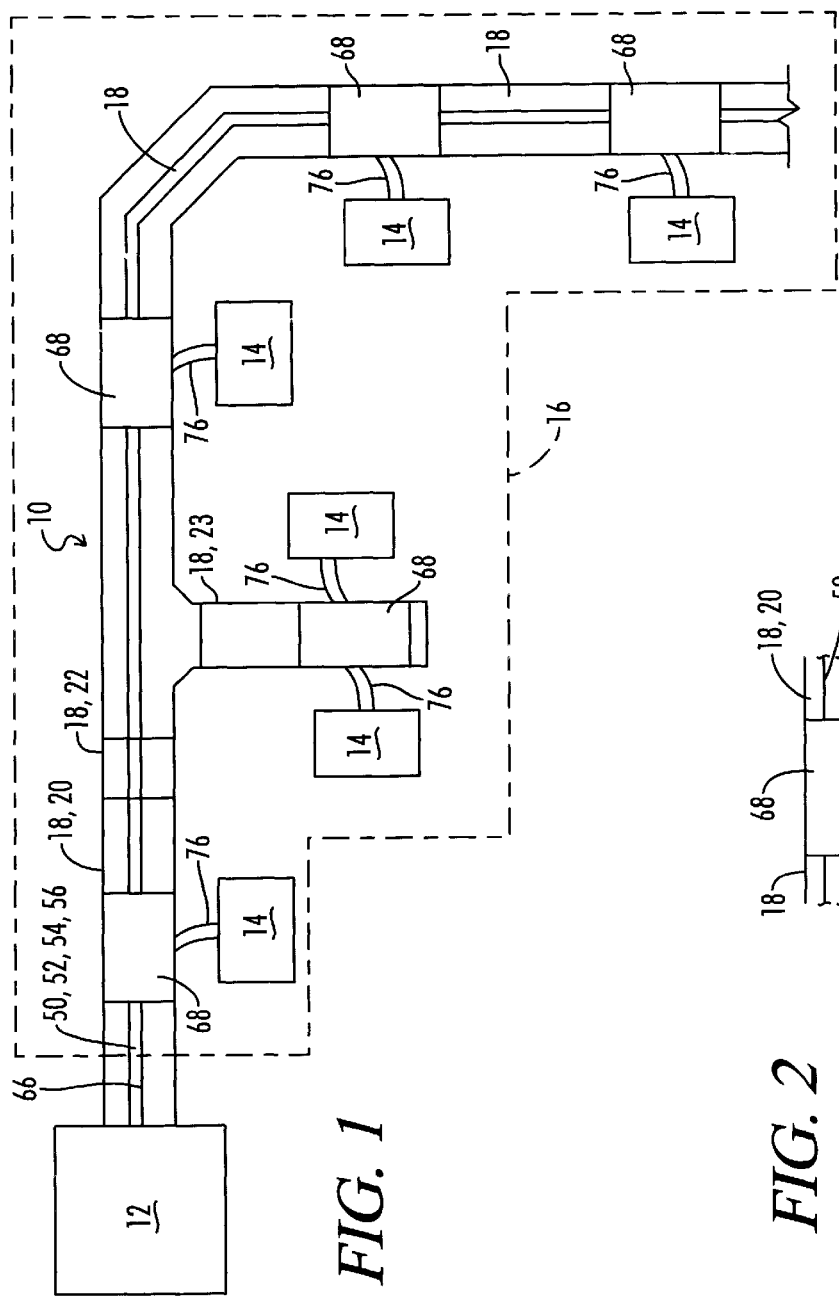
FIG. 1 is a schematic plan view of a modular fluid transport system in a dialysis clinic.

Referring now to FIG. 1, a fluid transport system is shown and generally designated by the numeral 10. The system 10 transports various fluids from a source 12 to a plurality of dialysis machines 14 in a dialysis treatment clinic 16.

The source 12 may either be a conventional built in place system for providing pure water and additives to the dialysis clinic, or more preferably it may be a portable system constructed in accordance with U.S. patent application Ser. No. 09/122,000 filed on Jul. 24, 1998, of Peterson, et al, entitled "Portable Water Treatment Facility", the details of which are incorporated herein by reference.

Source 12 is a system for producing water from a reverse osmosis purification system. It may also be a source of deionized water.

Those portions of the fluid transport system within the dialysis clinic 16 include a modular ductwork 18 which preferably is made of a plurality of removable interchangeable ductwork segments such as 20 and 22. Ductwork 18 may also be referred to as a conduit housing.

In order to enhance the modular nature of the system 10 and to minimize the time and labor required for assembly thereof, the longer length runs of the ductwork 18 will preferably be assembled from a plurality of substantially identical interchangeable standard length ductwork segments such as 20 and 22. In order make corners, and to provide vertical segments, various shaped interconnecting ductwork fittings will be provided. Additionally to complete some installations it will be necessary to use some custom fabricated components.

Figure 5:
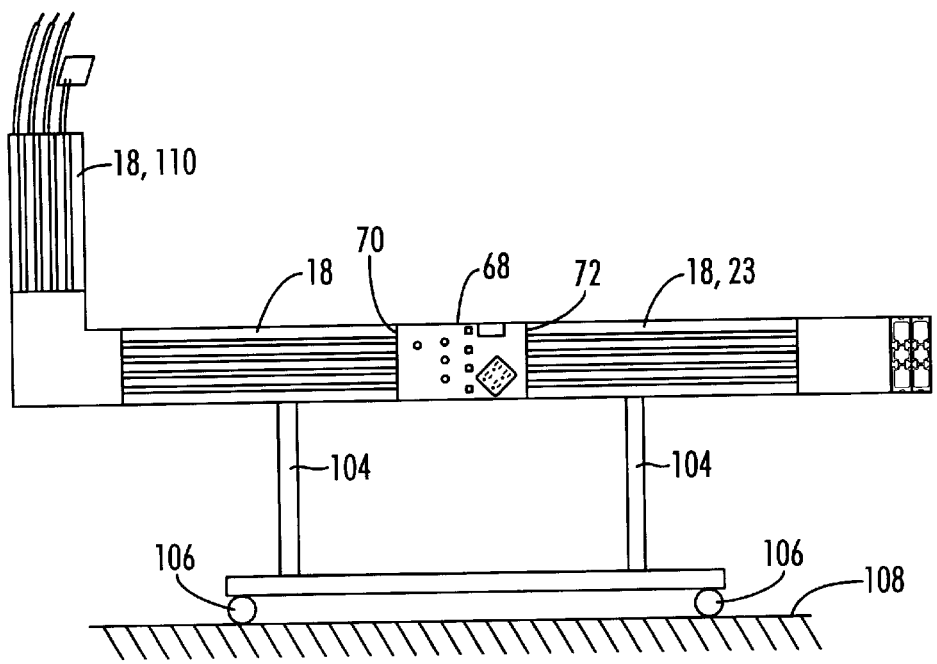
FIG. 5 is an elevation view of an interior run of the transport system of FIG. 1, showing supporting columns on lockable casters supporting the fluid transport system from the floor.
Figure 6:
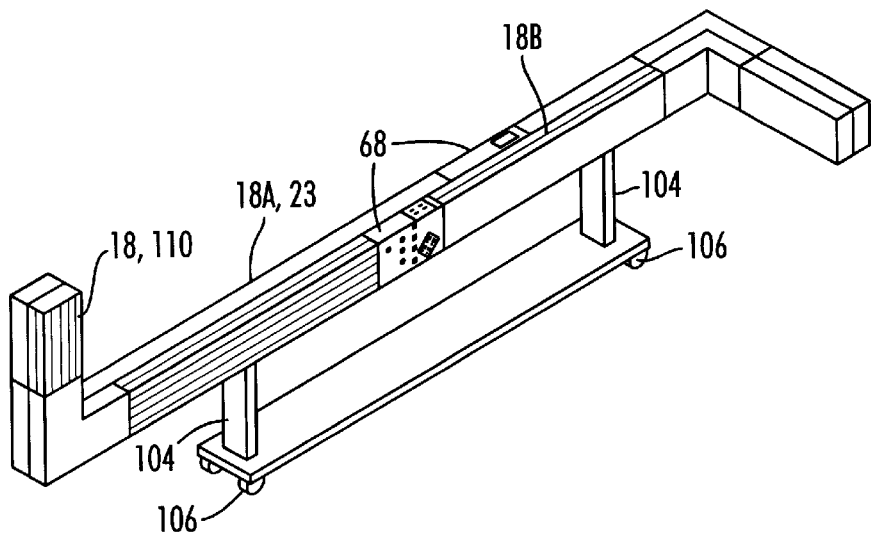
FIG. 6 is an isometric view of another interior fluid transport system portion having back to back ducts allowing connection of dialysis machines on either side of the ductwork system.

At least some of the ductwork segments such as 20 and 22 may be mounted on an interior face of a wall of the room which defines the clinic 16. Other ones of the ductwork segments such as 23 are free standing segments extending from the wall into the interior of the room. The details of construction of the free standing ductwork segments 23 are schematically illustrated in FIGS. 5 and 6. The free standing ductwork segments 23 are supported on portable columns or stands 104 having lockable casters 106 engaging a floor 108 of the room of the dialysis clinic 16. Also shown in FIG. 5 are vertical portions 110 of ductwork 18.

FIG. 6 illustrates two parallel runs of ductwork 18 placed back to back with their connecting stations 68 facing outward away from each other, so as to provide plumbing, electrical and telecommunication utilities to adjacent rows of dialysis machines 14 within the interior of the clinic. This is schematically illustrated in FIG. 1 by the two dialysis machines 14 schematically illustrated on opposite sides of the interior ductwork segment 23.

Figure 3:
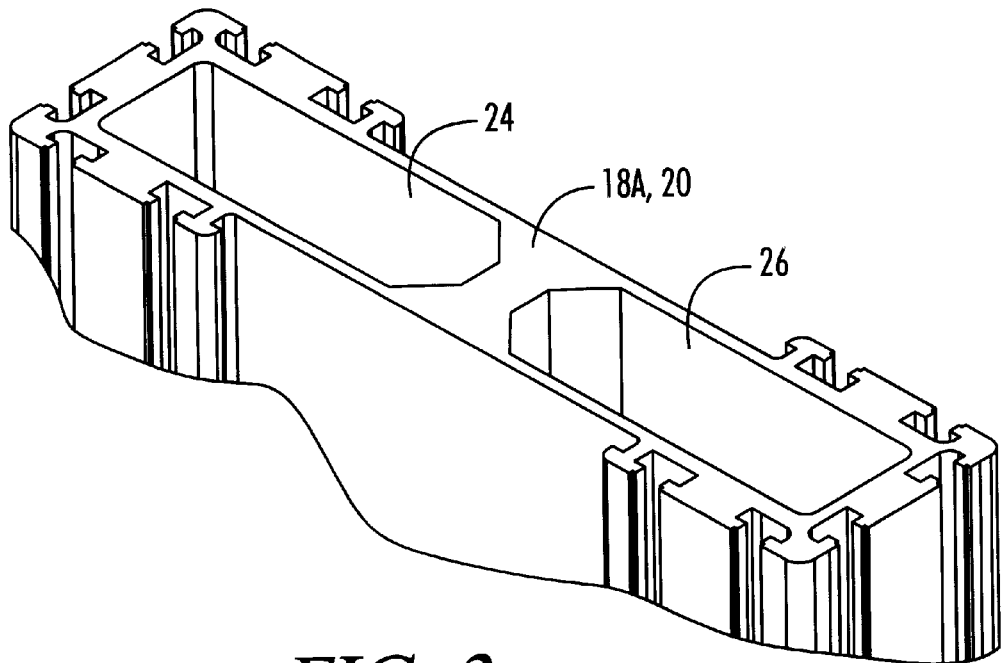
FIG. 3 is an isometric end view of one embodiment of ductwork segment.

FIG. 3 illustrates one embodiment 18A of the ductwork which is an extrusion having first and second cavities 24 and 26 extending there through. The extrusion may be formed from aluminum, plastic or other suitable material.

Figure 4:
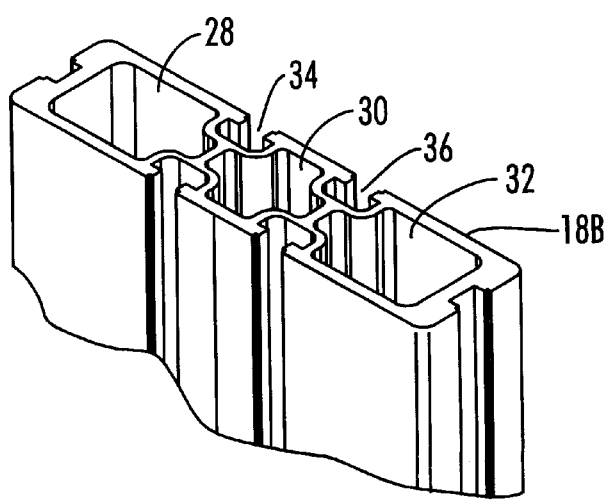
FIG. 4 is an isometric end view of another embodiment of ductwork segment.

FIG. 4 illustrates another embodiment 18B of the modular ductwork having first, second and third cavities 28, 30 and 32 defined there through.

Figure 11:
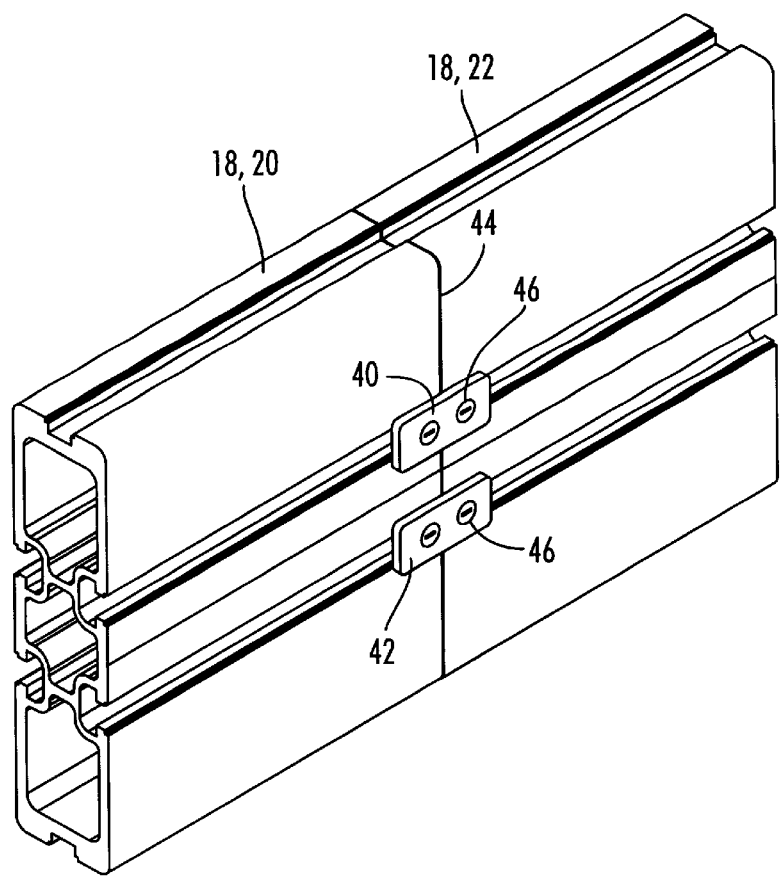
FIG. 11 is an isometric view of two adjacent ductwork segments of the system of FIG. 1, showing the manner in which the ductwork segments are structurally connected to each other.

FIG. 11 illustrates the manner in which two adjacent ductwork segments such as 20 and 22 may be structurally connected together.

The extruded structural duct shapes of FIGS. 3 or 4 include external channels such as 34 and 36. T-nuts 38 are slidably received in the channels 34 and 36. Connector straps 40 and 42 span the junction 44 between adjacent ductwork segments 20 and 22. Screws 46 extend through the straps 40 and 42 and threadedly connect with the T-nuts 38 so as to clamp the straps 40 and 42 in place.

Figure 12:
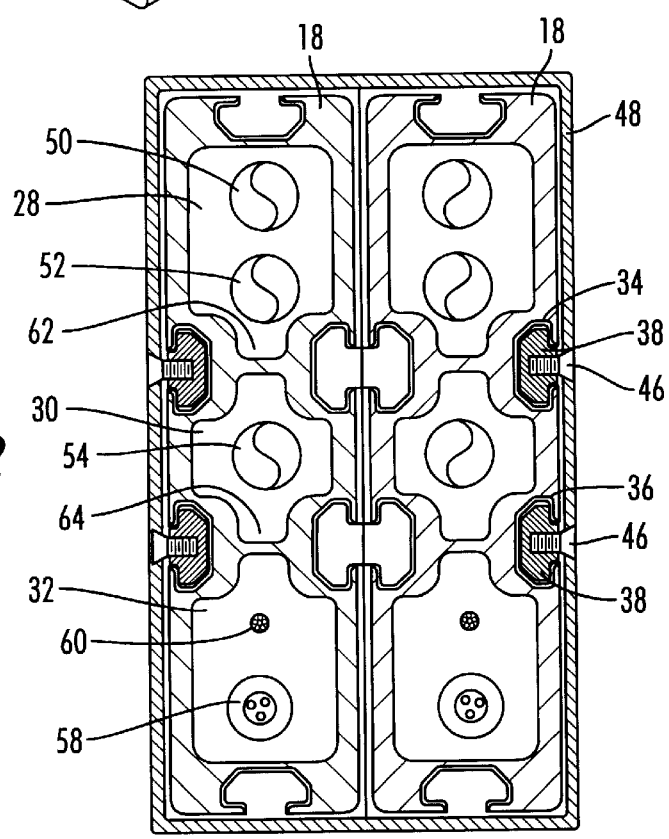
FIG. 12 is a cross-sectional view of two back to back ducts such as used in the system of FIG. 6, showing in cross-section the structural connecting devices.

FIG. 12 similarly illustrates two lengths of duct 18 which are running in parallel and which are supported from each other, in a manner analogous to that further described below with regard to FIG. 6. In the embodiment of FIG. 12, a strap 48 encircles the two parallel conduits 18, and the strap 48 is connected structurally to the conduits with T-nuts 38 and screws 46 in a manner like that described for FIG. 11.

The extruded ducts of FIGS. 11 and 12 also provide a structural support for various associated equipment, which may be hung from channels 34 and 36 using connectors like the T-nuts 38 and screws 46.

Figure 2:
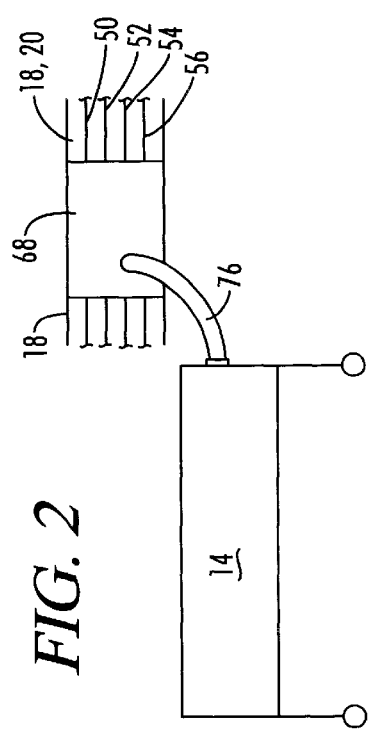
FIG. 2 is a schematic elevation view of a portion of the system of FIG. 1.

As seen in the elevation view of FIG. 2, the ductwork 18 preferably carries a plurality of generally parallel fluid conduits such as 50, 52, 54 and 56. For example, the first conduit 50 may carry purified water or dialysate from source 12. The second, third and fourth conduits 52, 54 and 56 may carry various additives for the water from the source 12 or storage tanks and may include a drain connection for the removal of effluents from the machine.

In the embodiment illustrated in FIG. 12, one possible arrangement of the conduits within the ductwork 18 is illustrated. In the embodiment of FIG. 12, the left-hand ductwork 18 carries two fluid conduits 50 and 52 in the upper cavity 28, a third fluid conduit 54 in the intermediate cavity 30, and a power cable 58 and communications cable 60 in the third cavity 32.

The cavities 28 and 30 which carry the fluid conduits 50, 52 and 54 may be described as including secondary containment chambers 62 and 64 for containing liquid which may leak from the fluid conduits 50, 52 or 54.

In the embodiment of FIG. 1, the conduits such as 50, 52, 54 and 56 may each be a continuous length of tubing which extends through at least two adjacent ductwork segments such as 20 and 22.

It will be understood that when the source 12 and the dialysis clinic 16 are separated by a substantial distance, such as when the source 12 is located on a different floor of the building or is otherwise located a substantial distance from the clinic 16, an initial segment 66 (See FIG. 1) of each of the fluid conduits may run freely through the walls, floors or other utility openings of the building, and need not be contained within the modular ductwork 18. These initial portions of conduit will preferably be relatively long lengths of flexible conduit, which are run from a spool of conduit.

Interspersed within the ductwork 18 are a plurality of connecting stations 68. The connecting stations 68 may also be referred to as connecting plates or outlet plates. The connecting stations 68 are fluidly connected to the fluid conduits such as 50, 52, 54 and 56 and also to the power cable 58 and communications cable 60.

Figure 7:
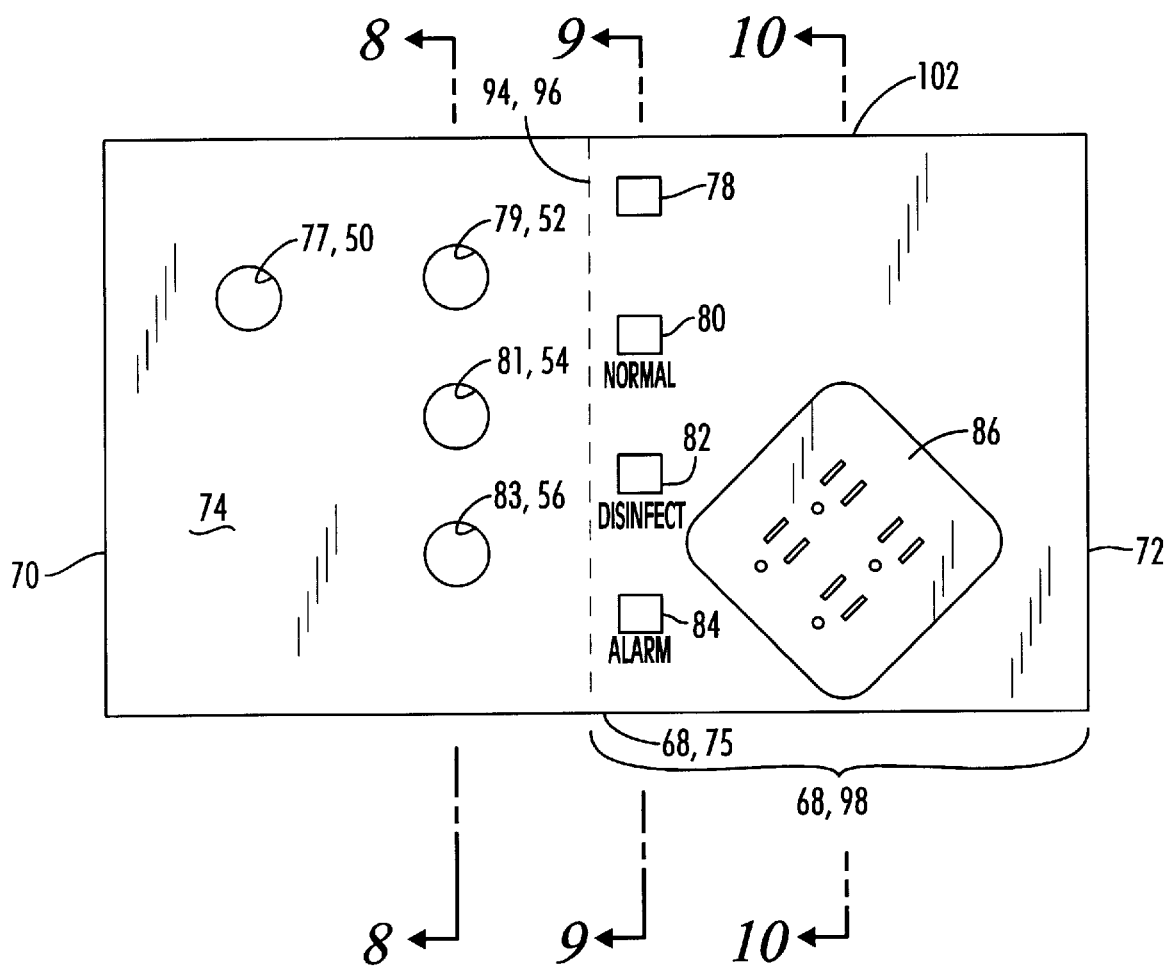
FIG. 7 is an enlarged view of one of the outlet plates at a dialysis connection station of the system of FIG. 1.

As been seen in FIG. 7, the connecting station 68 has first and second ends 70 and 72 and has a front surface 74. As best seen in FIGS. 5 and 6, the ends 70 and 72 are connected to the ductwork 18. The connecting station 68 includes a sheet metal outer housing 75 extending from first end 70 to second end 72. Contained within the housing 75 on the left portion thereof is a manifold block 94 as best seen in FIG. 7 which extends from left end 70 to a right end 96 of manifold block 94. A hollow housing portion 98 extends from right end 96 of manifold block 94 to the right end 72 of housing 75.

The various fluid conduits contained in the ductwork 18 are connected to passageways formed through the manifold block 94 of connecting station 68. The passageways typically are longitudinal bores extending from first end 70 to second end 96. A plurality of outlet ports such as 77, 79, 81 and 83 communicate with the passageways and thus communicate with the fluid conduits 50, 52, 54, 56 respectively. Quick connect couplings 100 (See FIG. 8) are mounted in the outlet ports 77, 79, 81 and 83 for connection of those ports to the dialysis machine 14 via a bundle of flexible hoses schematically indicated as 76 in FIGS. 1 and 2. It will be understood that the hoses of bundle 76 need not actually be bundled together, and they may be separate hoses.

Continuing with the description of the connecting station 68 at FIG. 7, the communications cable 60 is connected to communications outlet 78 which includes a quick connect adapter for connection of the dialysis machine 14. The data communications outlet 78 may be utilized to connect the dialysis station 14 to a monitoring device of a central monitoring system.

Various monitors associated with the connecting station 68 are connected to indicator lights such as 80, 82 and 84 which indicate whether the system is in a normal mode of operation, a disinfectant mode, or alarm mode. The disinfectant mode is indicated when hot water or chemical disinfectants are being flushed through the system. The alarm mode is illuminated when an abnormality in the operation of the system is detected.

The power cable 58 is connected to a power outlet 86 on the connecting station 68.

Figure 8:
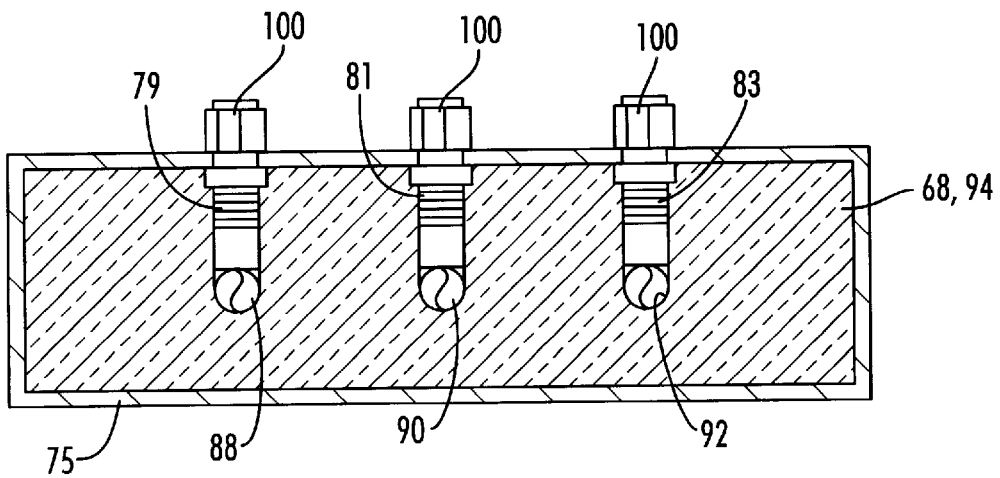
FIG. 8 is a schematic sectioned view showing the connection of some of the fluid outlets on the outlet plate of FIG. 7.
Figure 9:
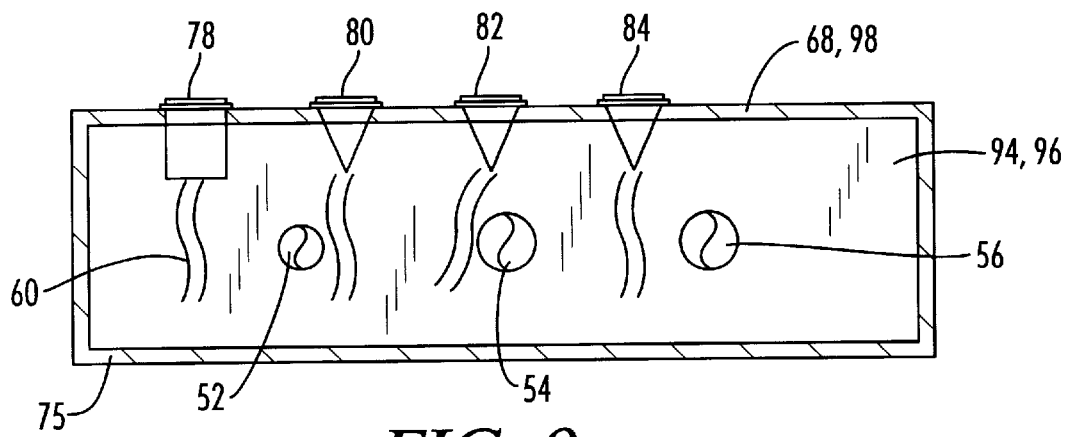
FIG. 9 is a schematic sectioned view showing the connection of some of the indicator lamps of the outlet plate of FIG. 7.

FIG. 8 is a schematic section view taken through the three outlet ports, 79, 81 and 83, and shows the same connected to three of the passageways through connector plate 68, which passageways are designated as 88, 90 and 92. As previously noted, the passageways 88, 90 and 92 typically extended from first end 70 to second end 96 of the manifold block 94, which is typically a solid block of a machineable material such as plastic. The passageways 88, 90 and 92 extend through the solid block 94 from first end 70 to the second end 96.

The hollow housing portion 98 of connecting station 68 contains the communications outlet 78, the indicator lights 80, 82 and 84, and the power outlet 86.

FIG. 8 only illustrates three passageways 88, 90 and 92. It will be understood that there will be additional passageways for each fluid conduit connected to the connector plate 68.

The fluid conduits such as 52, 54 and 56 are connected to the passageways 88, 90 and 92 at the first end 70 and second end 96 of the solid manifold block 94. The section views of FIGS. 9 and 10 through the hollow portion 98 of connecting station 68, schematically illustrate the fluid conduits 52, 54 and 56 which are connected to the passageways 88, 90 and 92 at the second end 96 of solid block portion 94.

Figure 10:
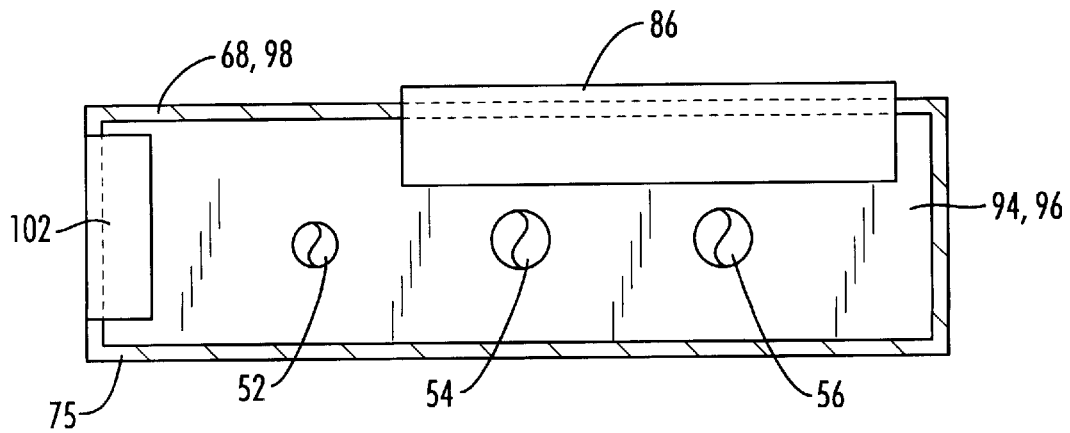
FIG. 10 is a schematic sectioned view showing the location of the electrical outlet of the outlet plate of FIG. 7.

As seen in FIG. 10, a second power outlet 102 may be mounted in the upper surface of the hollow housing portion 98 of connecting station 68. All outlets are integrally ground fault interrupt protected.

The various ductwork segments, such as 20, 22, 23 and connecting station 68 are releasably connected together to allow various components of the system 10 to be removed for service and disinfection. After removal, components such as the connecting station 68 and ductwork segments 20, 22 and 23 can be replaced by a like component while the replaced component is being disinfected or serviced.

The removability of the various components also aids in the ability to heat disinfect the components. Those components which are in communication with the fluids, and particularly the fluid conduits 50, 52, 54 and 56, are preferably constructed from a material which is stable at a temperature of at least 105 degrees Celsius applied for a period of at least twenty (20) hours to facilitate heat disinfection. Some suitable materials include polytetrafluoroethylene, polypropylene or cross-linked polyethylene tubing. In the preferred embodiment such tubing may be sterilized by autoclaving prior to use. It may also be sterilized by the transmission of heated fluid such as steam there through. It may also be chemically disinfected.

THE EMBODIMENT OF FIGS. 13–24

An alternative embodiment of the invention is illustrated in FIGS. 13–24. A representative portion of this alternative fluid transport system is shown in schematic elevation view in FIG. 13 and is generally designated by the numeral 122. Like the system 10 of FIG. 1, the fluid transport system 122 is designed to transport fluids from a source such as the source 12 to a fluid-requiring instrument such as the dialysis machines 14.

Figure 13:
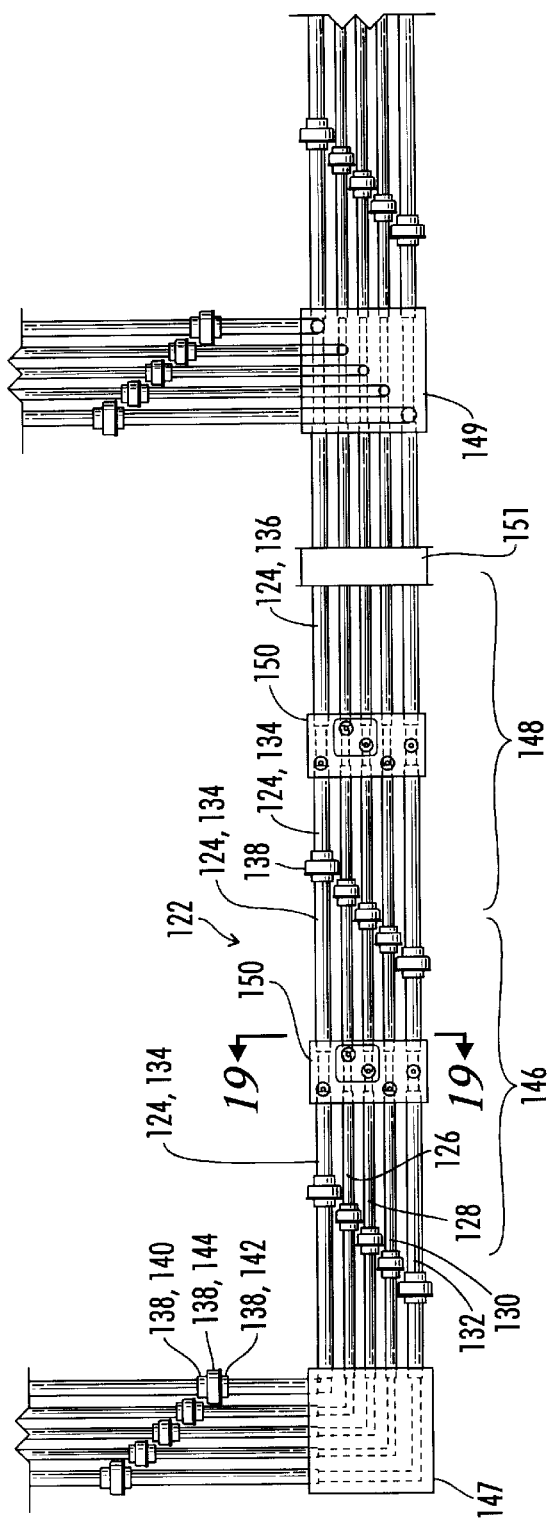
FIG. 13 is a schematic elevation view of an alternative embodiment of the fluid transport system.

There are several primary differences between the system 122 of FIG. 13 and the system 10 of FIG. 1. First, the system 122 primarily utilizes relatively short rigid plastic conduit segments which are connected together by detachable couplings, which preferably are unions. Second, the outer ductwork of the system 122 is preferably formed of sheet metal rather than the extruded shapes of FIGS. 3 and 4; it is noted, however, that the system 122 may also use extruded ductwork like that described for the system 10. Third, the connecting station has been greatly modified to provide for a rapid changeout of a dialysis machine. In FIG. 13, the ductwork is not shown, so that the details of construction of those components within the ductwork may be seen. The details of the ductwork are more clearly seen in the cross sectional view of FIG. 24.

The system 122 includes five fluid conduits 124, 126, 128 130 and 132. Each of these conduits, such as for example conduit 124, includes a plurality of removable conduit segments, such as adjacent segments 134 and 136 of the conduit 124. Adjacent conduit segments such as 134 and 136 are joined by a detachable coupling 138 which is a conventional union with o-ring seals. As will be understood by those skilled in the art, the union has first and second parts 140 and 142 which will be fixedly attached, such as by plastic welding, to the adjacent pipe segment, and a rotating collar 144 which is used to connect the parts 140 and 142 of the union.

Also shown in FIG. 13 are a typical elbow fitting 147 for making a right angle bend in the fluid transport system 122, and the typical T fitting 149.

Figure 14:
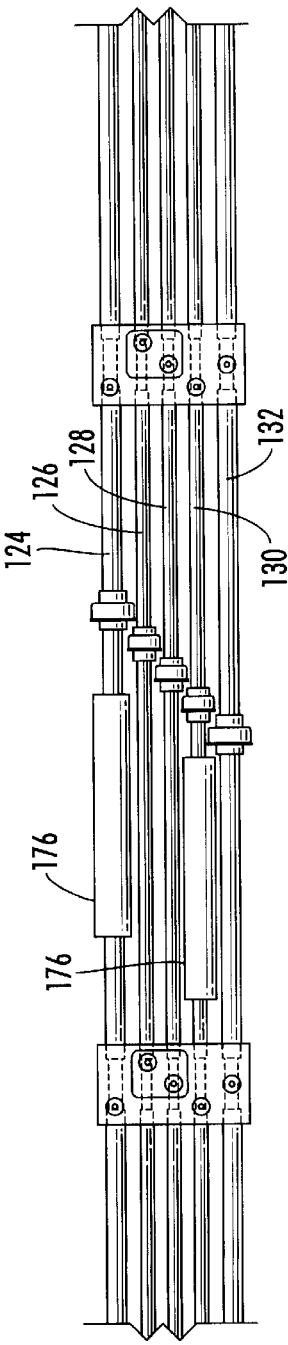
FIG. 14 illustrates a portion of the fluid transport system like that of FIG. 13, which includes an expansion joint in some of the fluid conduits.

FIG. 14 schematically illustrates a portion of the system of FIG. 13 with the addition of expansion joints 176 located in the first and fourth conduits 124 and 130.

Much of the fluid transport system 122 is defined by prefabricated standard interchangeable system modules such as indicated at 146 and 148.

Each system module such as 146 includes a conduit segment such as 134 for each of the fluid conduits 124 through 132. A detachable coupling such as 138 is attached to at least one end of each fluid conduit segment.

The modular system 10 or 122 of the present invention may provide modular piping segments such as 134 or modular ductwork segments such as 20 and 22 or combined modular piping and ductwork segments 146 in convenient lengths. For example, a typical modular element 146 may have a length of approximately eight feet. The pipe conduit segments 134 will have male or female union connections on either end. The ductwork segments will have attachments for interconnecting with adjacent ductwork segments.

There can be lengths of the system 122 in which the system modules 146 and 148 include only piping and no fluid connection stations for the dialysis machines, but in the operating portion of the dialysis clinic many of the system modules such as 146 and 148 will include a connecting station 150 for connection of one of the dialysis machines such as 14 shown in FIG. 2. The connecting stations 150 may also be referred to as connecting plates or outlet plates.

As was the case with the preferred materials for the system 10 of FIG. 1, each of the fluid conduits 124 through 132 is preferably constructed from materials which are stable at a temperature of at least 105 degrees Celsius supplied for a period of at least twenty (20) hours, so as to facilitate heat disinfection. Each of the fluid conduits, and particularly each of the removable conduit segments is preferably constructed from polytetrafluoroethylene, polypropylene, or cross-linked polyethylene.

It has been determined that these materials are superior for use in a hemodialysis clinic, because they are less likely to give off contaminating gases, or to leach undesirable materials such as fillers, plasticizers, stabilizers, etc., as compared to the typical prior material polyvinylchloride. The use of these materials allows heat sterilization of the conduits in place within the system 122. This may be accomplished by flowing hot fluids such as steam there through. This is particularly desirable for conduits used to conduct fluids in which bacterial growth is particularly a problem. In the case of a dialysis machine, this is particularly true for the first conduit 124 which typically conducts pure water and the fourth conduit 130 which may typically be used to conduct a bicarbonate solution.

Figure 24:
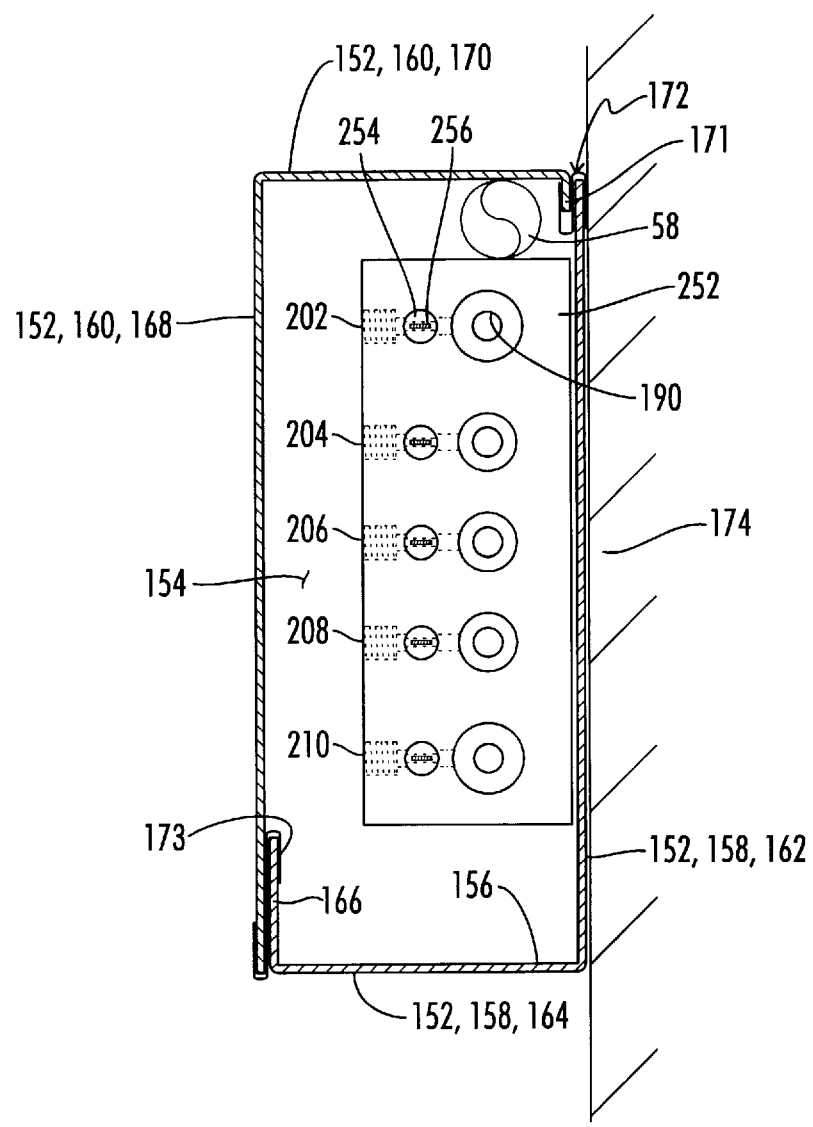
FIG. 24 is an elevation-sectioned view showing an alternative type of ductwork system within which the fluid transport system of FIG. 13 may be mounted. A universal manifold block is shown mounted within the ductwork. The manifold block of FIG. 24 is slightly modified as compared to the view seen in FIG. 16 of the manifold block.

Furthermore, each system module 146 and 148 will be associated with and supported within a segment of sheet metal ductwork such as the ductwork 152 shown in FIG. 24. Ductwork 152 may also be referred to as a conduit housing. At periodic intervals the conduits 124–132 are supported from the ductwork 152 by brackets such as 151.

The ductwork 152 defines a single containment passageway or chamber 154 in which all of the fluid conduits 124 through 132 are received. The lower portion 156 of the passage 154 may be defined as a secondary containment chamber 156 for catching any fluids leaking from the fluid conduits 124 through 132.

In the cross-sectional view of FIG. 24 it is seen that the ductwork 152 includes a base portion 158 and a cover portion 160. The base portion 158 includes a back wall 162 and a bottom 164 with an upward extending lip 166 to define the secondary containment chamber 156.

The cover portion 160 includes a front wall 168, a top 170 and a downward extending lip 171. The front wall 168 and lip 166 overlap and are held together by an S-shape clip 173 which runs along the length of ductwork 152. The lip 171 and back wall 162 overlap and are held together by an S-shape clip 172 which runs along the length of ductwork 152.

The base portion 158 of the ductwork 152 is mounted on a support 174 which may be a wall of the room, or which may be a vertical column support such as support 104 seen in FIGS. 5 and 6.

At intervals along the length of the conduits 124, 126, 128, 130 and 132, those conduits are supported from the back wall 162 by brackets such as bracket 151 seen in FIG. 13.

The ductwork 152 is preferably formed in prefabricated segments corresponding to the length and dimensions of the system modules 146 and 148. Those prefabricated segments may come in several pieces so as to allow the fitting of the ductwork with the connecting stations 150. The ductwork 152 may include openings and access panels associated with the connecting stations 150 and with other components.

Figure 25:
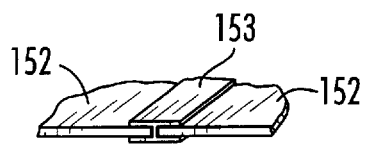
FIG. 25 is a schematic view of the end connection between adjacent ductwork segments.

The ends of the pre-fabricated segments are joined together by H-shape clips 153 as shown in FIG. 25.

Figure 19:
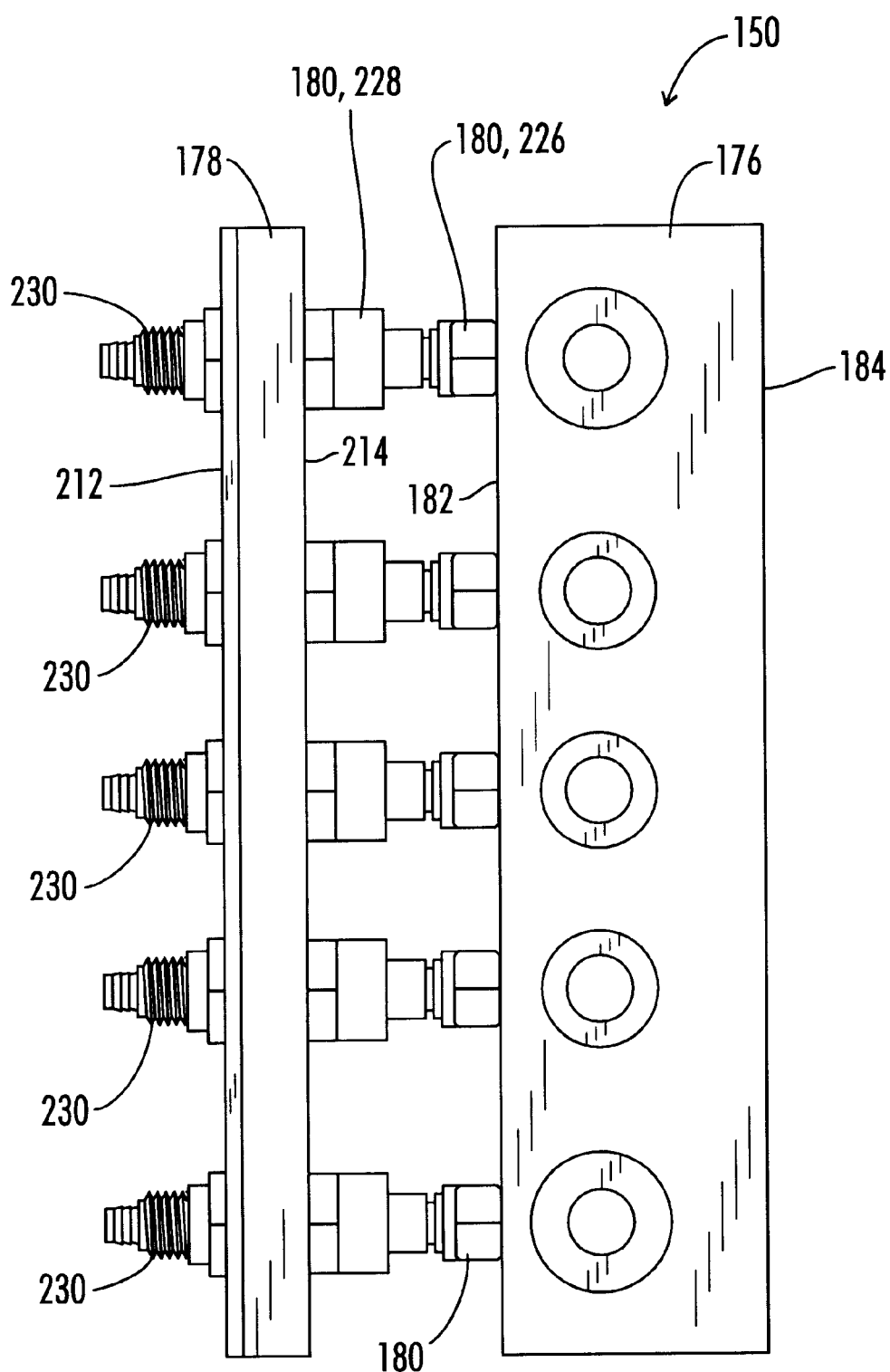
FIG. 19 is a side elevation view of the interface manifold block of FIG. 17 mounted on the universal manifold block of FIG. 15.

The details of construction of the connecting station 150 are best seen in the side elevation view of FIG. 19 which is a view taken along line 19—19 of FIG. 13. The connecting station 150 includes a first manifold block 176 which is directly connected to the conduits 124 through 132, and a second manifold block 178 which is detachably connected to first manifold block 176 by first plurality of quick connect couplings 180.

The first manifold block 176 may also be referred to as a connector plate or outlet plate. The second manifold block 178 may also be referred to as an adapter plate.

Figure 15:
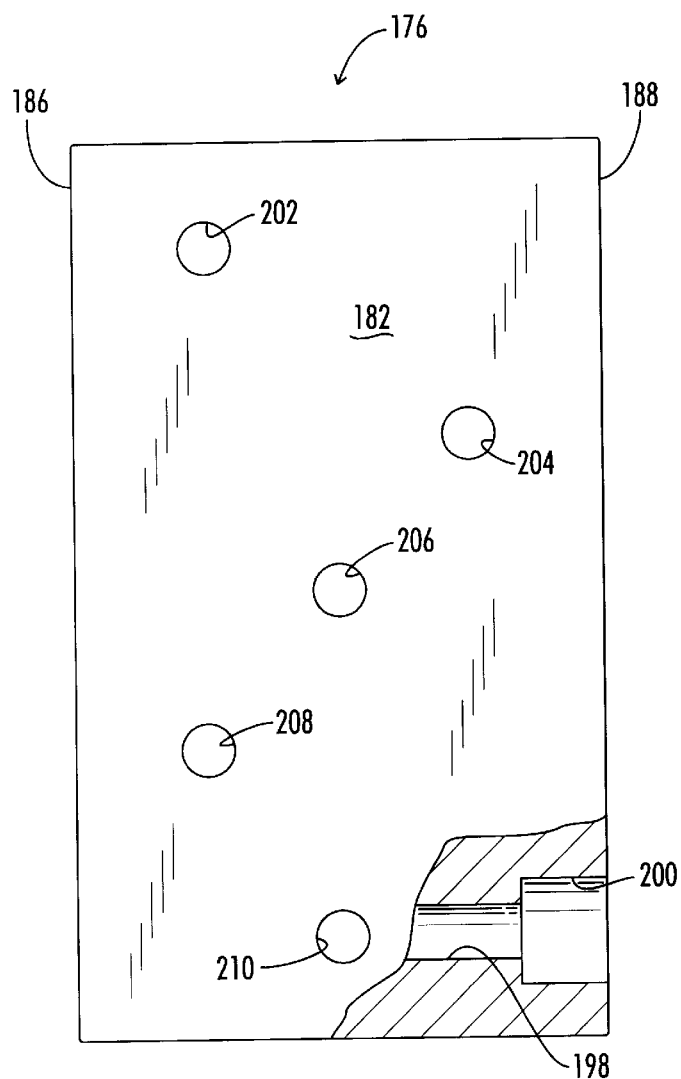
FIG. 15 is an elevation view of a universal manifold block to which the conduits of the system of FIG. 13 are directly connected.
Figure 16:
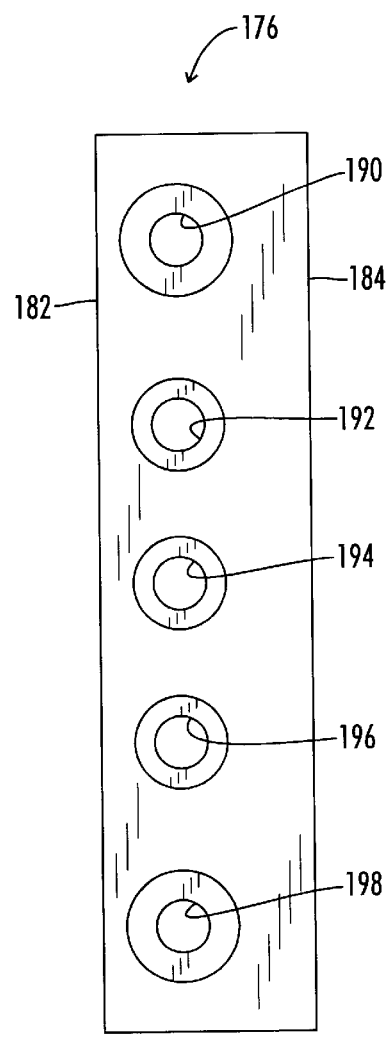
FIG. 16 is a right side elevation view of the universal manifold block of FIG. 15.

The details of construction of the first manifold block 176 are best shown in FIGS. 15 and 16. Manifold block 176 is preferably constructed from a rectangular block of solid plastic material, preferably the same material from which the fluid conduits are constructed. The manifold block 176 has front and rear surfaces 182 and 184, and has first and second end surfaces 186 and 188.

A plurality of supply passages 190, 192, 194, 196 and 198 extend in a parallel fashion through the block of material from the first end 186 to the second end 188. Adjacent each of the end walls 186 and 188 a counter bore such as 200 defines a socket 200 for receiving and end of an associated one of the fluid conduits 124 through 132. The fluid conduits 124 through 132 are preferably connected to the first manifold block 176 by heat welding or other suitable technique to provide a rigid and permanent attachment.

The connections between the piping and the sockets 200 on the manifolds such as 176 or the union fittings 138 are preferably formed by socket fusion welding. Socket fusion welding is a technique by which the plastic is heated to the melting point within heating dies, and then the components to be joined are forced together. This technique is preferred because the potential for forming interstitial spaces, voids, cracks, etc., is minimized or eliminated altogether. Voids and cracks constitute sites for potential bio-growth and make dis-infection difficult.

Each of the supply passages 190 through 198 tees into a short laterally extending portion intersecting the front surface 182, which may be referred to as an interface surface so as to define a first plurality of interface ports 202, 204, 206, 208 and 210 on the front surface 182.

Figures 17, 18:
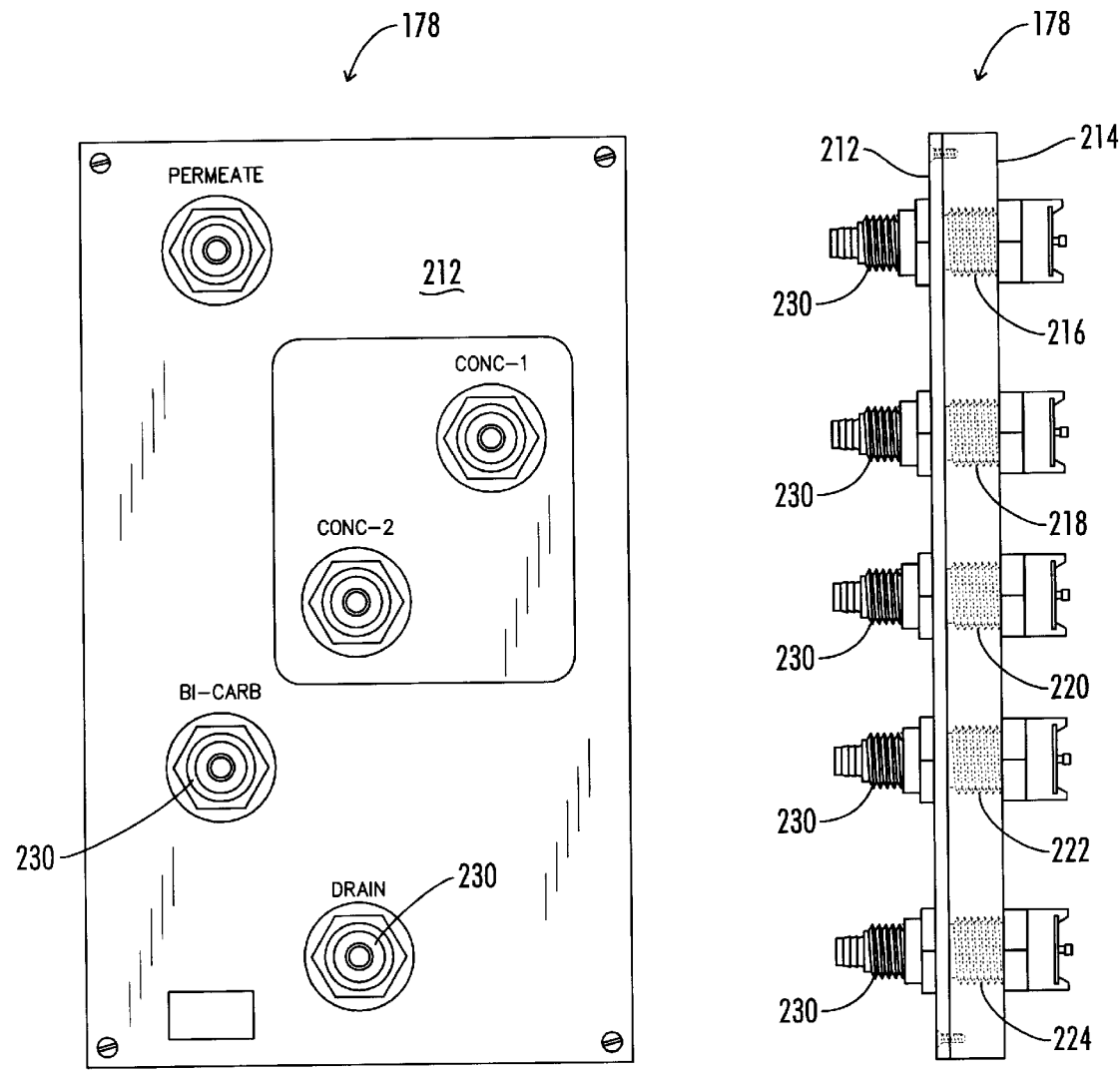
FIG. 17 is a front elevation view of an interface manifold block constructed to be quick connected to the universal manifold plate of FIG. 15.
FIG. 18 is a right side elevation view of the interface manifold block of FIG. 17.

The second manifold block which is 178 is best shown in the front and side views of FIG. 18. Second manifold block 178 has a front surface 212 and a rear surface 214. The rear surface 214 may be referred to as a second interface surface 214, and the front surface 212 may be referred to as an outlet surface 212.

The first manifold block 176 may be referred to as a universal manifold block 176, and the second manifold block 178 may be referred to as an interface manifold block 178.

The second manifold block 178 has a plurality of intermediate passages such as 216, 218, 220, 222 and 224 defined therethrough from the rear surface 214 to the front surface 212. Each of the intermediate passages 216 through 224 intersects the rear surface 214 at one of a second plurality of interface ports which are complementary to and aligned with the ports 202 through 210.

The first plurality of quick connect couplings 180 each include a first part 226 which is threadedly connected into one of the ports 202 through 210 of first manifold block 176, and a second part 228 which is threadedly connected to the corresponding port in the second manifold block 178.

The quick connect couplings 180, may for example be those manufactured and sold under the Parker, Colder, or Walther Prezision brands.

Those skilled in the art will be familiar with such couplings and will understand that they allow the second manifold block 178 to be quickly disconnected from the first manifold block 176 without the loss of fluids from the fluid passages 190 through 198. As the quick disconnects 180 are disconnected, spring-loaded valves contained in each of the parts 226 and 228 close the flow passage there through.

Additionally, a plurality of threaded hose fittings 230 (see FIG. 19) are connected to the front surface 212 of the second manifold block 178 to provide for connection to the hoses of the hose bundle 76 from the dialysis machine 14.

The hose interface manifold block 178 is not specific to any particular type of dialysis machine. Two additional examples of substitute second manifold blocks, specifically designed for use with specific dialysis machines, are shown in FIGS. 20 through 23.

Figure 20:
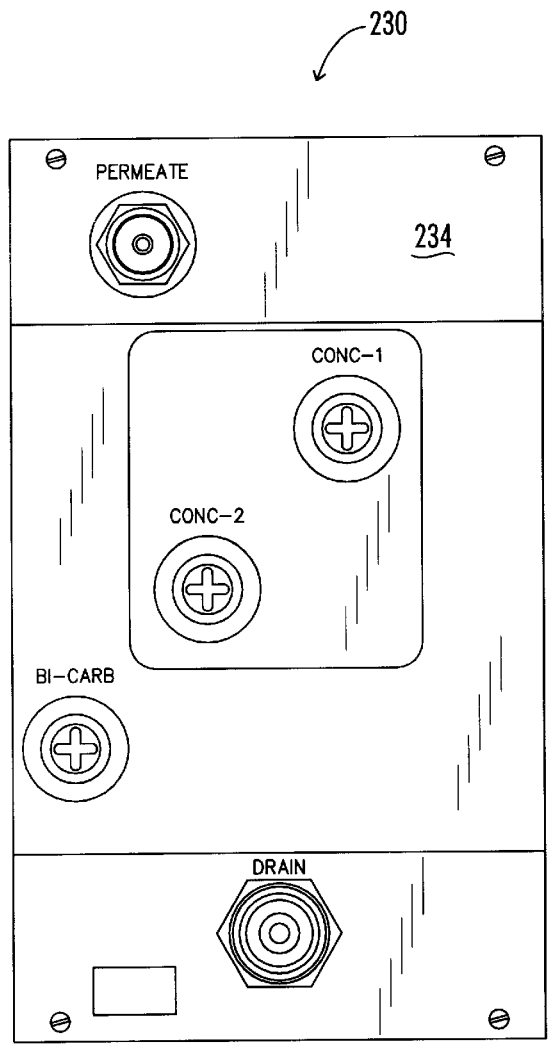
FIG. 20 is a front elevation view of a second interface manifold block which is specifically designed for connection to one particular type of dialysis machine.
Figure 21:
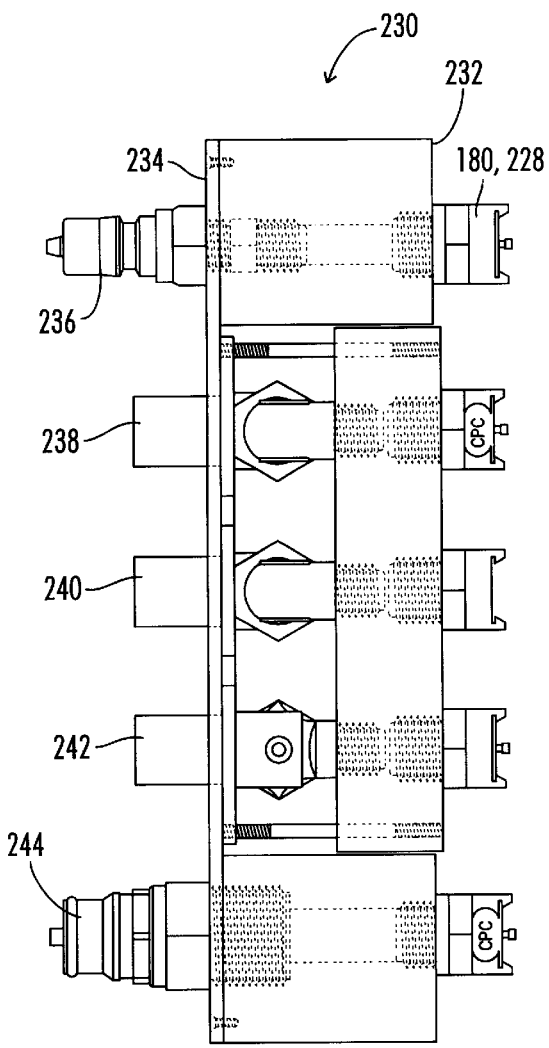
FIG. 21 is a schematic elevation sectioned view of the interface manifold block of FIG. 20.

FIGS. 20 and 21 are front and side elevation views, respectively, analogous to FIG. 17 and 18, of an interface manifold block 230 particularly designed for use with a Cobe brand dialysis machine. It is noted that on the back surface 232 of the interface manifold block 230, there are found the second parts 228 of quick connect couplings 180 which are identical in construction and arrangement as the second part 228 of couplings 180 shown in FIG. 19. Thus, the substitute interface manifold block 230 may be substituted for the interface manifold block 178 by merely disconnecting the quick connect couplings 180 shown in FIG. 19, and then reconnecting the interface manifold block 230 of FIG. 21 in place of the original interface manifold block 178.

The front surface 234 of the substitute interface manifold block 230 carries various fittings such as 236, 238, 240, 242 and 244 which are specifically constructed for connection to the Cobe brand dialysis machine.

Figures 22, 23:
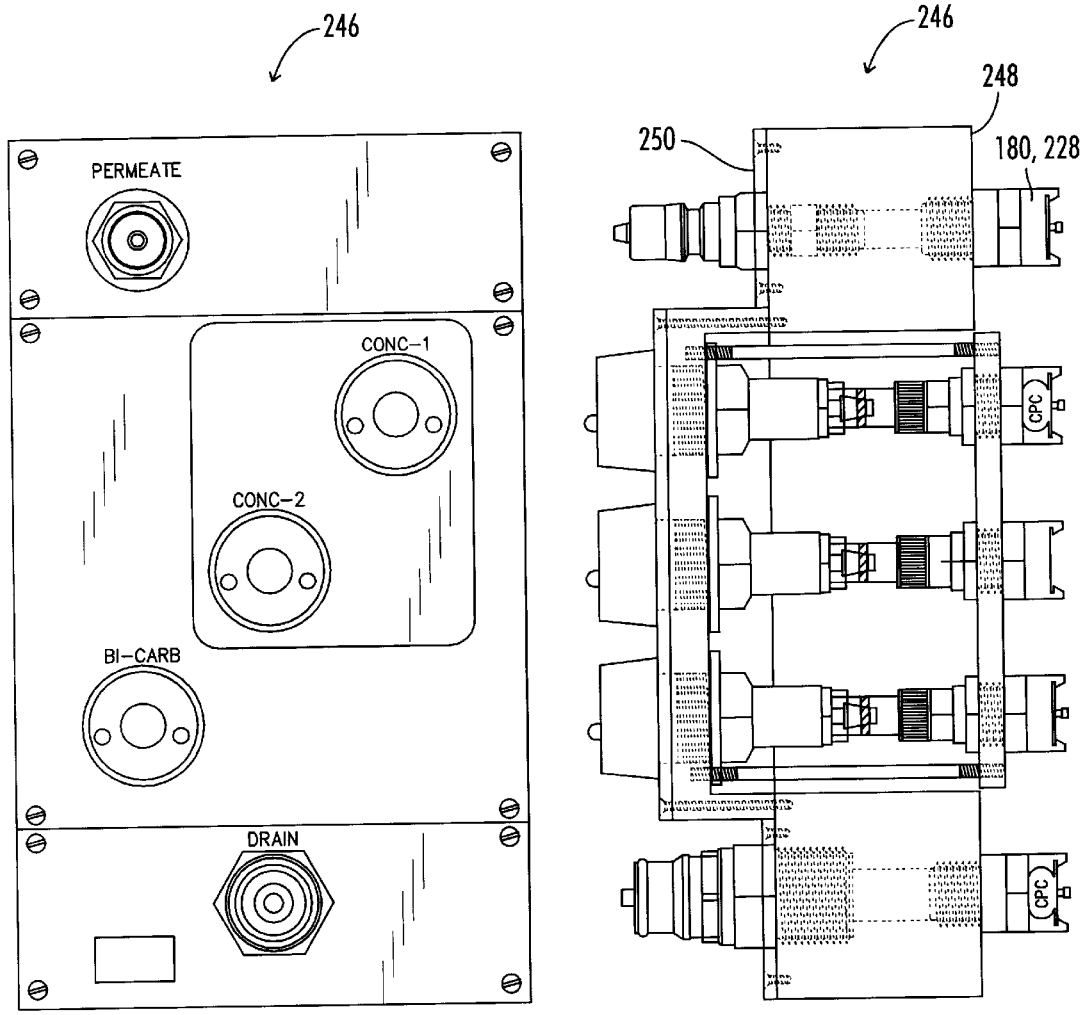
FIG. 22 is a front elevation view of still another interface manifold block designed for use with another specific type of dialysis machine.
FIG. 23 is a schematic elevation sectioned view of the manifold plate of FIG. 22.

FIGS. 22 and 23 show front and side elevation views of yet another machine specific interface manifold block 246 particularly designed for use with an Althin brand dialysis machine. Again, the interface manifold block 246 carries quick connect coupling portions 180, 228 on its rear surface 248, which will interconnect the couplings on the universal manifold block 176. Again, the front surface 250 carries a plurality of machines specific quick connect couplings designed for use with the Althin machine.

It is noted that FIGS. 21 and 23 are not true side elevation or section views, but instead they schematically illustrate the specific structure of the various couplings which are attached to the interface manifold block 230 or 246.

A connecting station like station 150 shown in FIG. 19 including the first and second manifold blocks 176 and 178 with the quick connect couplings 180 therebetween provides several advantages.

Primarily, it allows the dialysis machine 14 to be exchanged for a different dialysis machine 14 of a different make and model. Those skilled in the art will understand that each given make and model of dialysis machine typically has associated therewith its own machine specific group of quick connect couplings which are used to connect the dialysis machine to a station of a dialysis clinic. Two examples of different dialysis machines are the Cobe machine associated with the connectors of FIGS. 20 and 21, and the Althin machine associated with the connectors of FIGS. 22 and 23. In the prior art, a connecting station for a dialysis machine has typically been permanently installed in a rigid permanent wall and is suitable for connection only to one type of dialysis machine. If the machines used in a given clinic are changed, the entire system must be shut down and replumbed to provide suitable connections for the new machines.

With a connecting station like that shown in FIG. 150, the secondary manifold blocks 178 may be constructed in a form which are specific to a given make and model of dialysis machine. The first manifold block 176, however, is a universal design which need not ever be changed.

If it is desired to change the type of dialysis machine being utilized, all that need be done is to remove the second manifold block 178 by disconnecting the quick connect couplings 180 and to replace the second manifold block 178 with another second manifold block which has quick connect couplings on its front surface 212 particularly designed for use with the new dialysis machine.

This construction for the connecting station 150 eliminates what are known as "dead legs" within the piping system. Industry standards provide that in order to eliminate areas within the plumbing where fluids do not readily flow and bacteria may grow in stagnant fluid, there should be no portions of the conduit passageways in excess of five pipe diameters in length which do not have free flowing fluid therethrough. The use of the primary and interface manifold blocks with the quick connect couplings therebetween provides a manner of communication between the dialysis machine 14 and the fluid conduits which eliminates the presence of any such dead legs of greater than 5 pipe diameters in length. Furthermore, all of the components of the connection station may be readily removed and sterilized then replaced.

In FIG. 24 a slightly modified version of the universal manifold block 176 is shown and generally designated by the numeral 252. The manifold block 252 is similar to the manifold block 176 except for the addition of inline shut off valves such as 254 which lead from the passageways such as 190 to the outlet port such as 202. The shut off valves 254 are simple 90 degree valves which are operated with a flat end screwdriver which may be inserted into slot 256.

In FIG. 24, the interface manifold plate 178 has not been shown, but it will be understood that it is mounted on the manifold block 252 in the same manner as shown in FIG. 19. The front wall 170 of the sheet metal ductwork 152 will have an appropriate cut out opening therein through which the front surface of the interface manifold block 178, 230 or 246 with its associated fittings may extend for connection to the dialysis machine 14.

Also shown in FIG. 24 is the preferred location for the electrical power cable 58. The communications cable 60 is also preferably located in the general area of the power cable 58.

MANNER OF INSTALLATION, OPERATION AND USE

Either of the modular fluid transport systems 10 or 122 are designed to be pre-fabricated at an off site manufacturing facility and then transported to and installed within the dialysis clinic 16. Thus the modular fluid transport system 10 or 122 will in fact be sold as a piece of equipment and will not be permanently installed as part of the building structure. In addition to providing many advantages regarding cost, quality control, maintenance and the like, there are tax advantages to the purchase of depreciable equipment rather than the construction of the fluid transport system as a permanent part of the building.

Both the ductwork and the fluid conduits, and the various components such as the connecting stations 68 or 150 are prefabricated, and then brought to the site of the clinic 16 where they may be quickly assembled into the systems previously described.

By use of the preferred materials for the fluid conduits, the system may be heat sterilized in place by flowing steam or other hot fluids there through. Additionally, any particular portion of the system may be readily removed for off site sterilization.

Repair of any portion of the system 10 or 122 is easily accomplished by simply removing and replacing the effected components.

Also as previously described with regard to the connecting station 150, use of that arrangement allows the dialysis machines 14 to be easily exchanged for different models and makes of machines.

The use of the system 10 or 122 also provides great flexibility in the arrangement of the dialysis machines 14 within the clinic 16. With prior art built in place systems, this was not possible without tearing down walls, modifying or replacing chaises and replumbing a system. With the system of the present invention, the plumbing and outlets may be quickly rearranged by merely changing out various components.

Although the systems 10 and 122 have been particularly described for use with a dialysis clinic, it will be appreciated that many of the features of the present invention may be readily applied to other systems in which it is necessary to provide very pure fluids to an instrument which uses the fluids. For example, such systems could be utilized to provide medical gases. Such systems could be utilized in the semi-conductor manufacturing industry. Such systems can be utilized in the pharmaceutical manufacturing industry. In any industry where it is desirable to be able to thoroughly sterilize a plumbing system, the modular plumbing system of the present invention may find use.

Thus it is seen that the apparatus of the present invention readily achieves the ends and advantages mentioned as well as those inherent therein. While certain preferred embodiments have been illustrated and described for purposes of the present disclosure, numerous changes in the arrangement and construction of parts and steps may be made by those skilled in the art, which changes are encompassed within the scope and spirit of the present invention as defined by the appended claims.

What is claimed is:

1. A method of installing a fluid transport system of a dialysis clinic, comprising:
    a) fabricating a plurality of system modules at an off-site location, each module including a plurality of conduit segments having detachable couplings on at least one end, and a support for the conduit segments;
    b) transporting the modules to a clinic site;
    c) assembling the modules at the clinic site by connecting adjacent conduit segments of adjacent system modules with the detachable couplings; and
    d) connecting a plurality of dialysis machines to the fluid transport system; wherein step (a) includes providing some of the system modules with a connecting station including a first manifold block, a second manifold block and a plurality of quick connect couplings connecting the first and second manifold blocks; and step (d) includes connecting each of the dialysis machines to the second manifold block of one of the connecting stations.

2. The method of claim 1, wherein:
    step (a) includes providing each of the connecting stations with a second plurality of quick connect couplings attached to the second manifold block; and
    step (d) includes connecting each of the dialysis machines to the associated second manifold block with the associated second plurality of quick connect couplings.

3. The method of claim 2, further comprising:
    removing one of the dialysis machines and its associated second manifold block and second plurality of quick connect couplings; and
    replacing the removed dialysis machine with a replacement dialysis machine, a replacement second manifold block, and a replacement second plurality of quick connect couplings.

4. The method of claim 1, wherein:
    step (a) includes providing each of the system modules with a ductwork segment within which the plurality of conduit segments is received; and
    step (c) includes connecting adjacent ductwork segments.

5. The method of claim 1, wherein the system modules are free of any dead legs of length greater than five pipe diameters.

6. A method providing instrument-specific fluid connection to a hemodialysis machine, said method comprising:
    a) supplying fluids from a fluid supply source to a fluid outlet through a plurality of fluid conduits fluidly connected between the fluid supply source and the fluid outlet;
    b) connecting a first adapter plate to the fluid outlet with a first plurality of quick-connect fittings;
    c) connecting a first hemodialysis machine to the first adapter plate with a second plurality of quick-connect couplings;
    d) disconnecting the first hemodialysis machine from the first adapter plate by releasing the second plurality of quick-connect couplings;
    e) disconnecting the first adapter plate from the fluid outlet by releasing the first plurality of quick-connect couplings;
    F) connecting a second adapter plate to the fluid outlet with a third plurality of quick-connect couplings; and
    g) connecting a second hemodialysis machine to the second adapter plate with a fourth plurality of quick-connect couplings thereby replacing the first hemodialysis machine without interrupting fluid flow through the conduits.

7. The method of claim 6, wherein:
    the first and second hemodialysis machines use different kinds of connectors, and the fourth plurality of quick-connect couplings are of different design then the second plurality of quick-connect couplings.

8. The method of claim 6, wherein the fluid outlet, the first adapter plate, and the first and second pluralities of quick-connect couplings are free of any dead legs of length greater than five pipe diameters.

* * * * *